US 6,675,038 B2

(12) United States Patent
Cupples et al.

(10) Patent No.: US 6,675,038 B2
(45) Date of Patent: Jan. 6, 2004

(54) METHOD AND SYSTEM FOR RECORDING PROBE POSITION DURING BREAST ULTRASOUND SCAN

(75) Inventors: Tommy Earl Cupples, Columbia, SC (US); Donald Chin, Palo Alto, CA (US); Karen D. Maroc, San Jose, CA (US)

(73) Assignee: U-Systems, Inc., San Jose, CA (US)

( * ) Notice: Subject to any disclaimer, the term of this patent is extended or adjusted under 35 U.S.C. 154(b) by 134 days.

(21) Appl. No.: 09/854,654

(22) Filed: May 14, 2001

(65) Prior Publication Data

US 2002/0167549 A1 Nov. 14, 2002

(51) Int. Cl.[7] ................................. A61B 5/05
(52) U.S. Cl. ..................................... 600/424
(58) Field of Search ................. 600/424, 463, 600/426, 437, 443; 382/113, 278; 128/916

(56) References Cited

U.S. PATENT DOCUMENTS

| 5,398,691 | A | * | 3/1995 | Martin et al. ............... 600/463 |
| 5,572,999 | A | * | 11/1996 | Funda et al. ............... 600/118 |
| 5,795,297 | A | | 8/1998 | Daigle |
| 5,906,578 | A | * | 5/1999 | Rajan et al. ............... 600/424 |
| 5,971,923 | A | | 10/1999 | Finger |
| 6,063,030 | A | | 5/2000 | Vara et al. |
| 6,142,946 | A | | 11/2000 | Hwang et al. |
| 6,159,150 | A | | 12/2000 | Yale et al. |
| 6,171,244 | B1 | | 1/2001 | Finger et al. |
| 6,500,118 | B1 | * | 12/2002 | Hashimoto ................. 600/437 |

OTHER PUBLICATIONS

U.S. application Ser. No. 09/224,635 filed Dec. 31, 1998.
U.S. application Ser. No. 09/449,095 filed Nov. 24, 1999.
U.S. application Ser. No. 09/571,197 filed May 16, 2000.

* cited by examiner

Primary Examiner—Dennis Ruhl
Assistant Examiner—Ruby Jain
(74) Attorney, Agent, or Firm—Cooper & Dunham LLP (57) ABSTRACT

A method, system, and computer program product for providing textual ultrasound probe position information corresponding to an ultrasound image of a target is described. Based on a user's graphical manipulations of a probe icon relative to a breast icon, a text sequence corresponding to the user's estimate of the position of an ultrasound probe is automatically generated. User error and fatigue are reduced because manual keying of the probe position text sequence is no longer required, and the resulting outputs are standardized in format and therefore more amenable to archiving and electronic analysis. In one preferred embodiment, the user is permitted to select a snapping mode of operation in which the probe icon is snapped to align with a major direction of a preselected coordinate system, further enhancing ease-of-use and reducing user fatigue.

30 Claims, 6 Drawing Sheets

Right BR, Radial, 2:00, 4 cm

FIG. 3B

Right BR, Radial, 2:00, 8 cm

FIG. 3C

Right BR, Radial, 2:00, 14 cm

FIG. 3D

Left BR, Radial, 10:00, 9 cm

METHOD AND SYSTEM FOR RECORDING PROBE POSITION DURING BREAST ULTRASOUND SCAN

FIELD

This patent specification relates to medical ultrasound imaging systems. In particular, it relates to an easy-to-use user interface that promotes consistent and reliable recordation of probe position during a breast ultrasound scan.

BACKGROUND

Ultrasound imaging systems have become increasingly popular for use in medical diagnosis because they are non-invasive, easy to use, capable of real-time operation, and do not subject patients to the dangers of electromagnetic radiation. Instead of electromagnetic radiation, an ultrasound imaging system transmits sound waves of very high frequency (e.g., 1 MHz to 15 MHz) into the patient and processes echoes scattered from structures in the patient's body to derive and display information relating to these structures.

Ultrasound imaging systems have been increasingly used in breast cancer screening, detection, treatment, and research. Most commonly, a breast ultrasound procedure involves the placement of an ultrasound probe over a region of interest of the breast, with the radiologist or other medical professional (hereinafter "user") simultaneously viewing a real-time ultrasound image output on a computer monitor. The monitor also usually displays relevant text and/or graphical information near the ultrasound image for simultaneous viewing by the user. The user then presses a button to freeze the display, at which time the display may be printed on a printer or stored in digital format for later viewing and analysis.

Because much downstream analysis, interpretation, and decisionmaking may be performed based on the printed or stored information, it is crucial to ensure that the text annotation and/or graphical information relevant to the ultrasound image be both correct and properly formatted. As PACS (picture archiving and communication systems) and teleradiology (i.e., the calling up of archived images from remote locations by telephone line or internet connection) continue to increase in importance, the accurate and consistent annotation of ultrasound and other medical images will become increasingly important. Additionally, it is expected that accurate and consistent annotation of ultrasound and other medical images will become increasingly important as historical archives of breast ultrasounds and other medical images are built up over time for statistical analysis or other research purposes.

Figure 1:
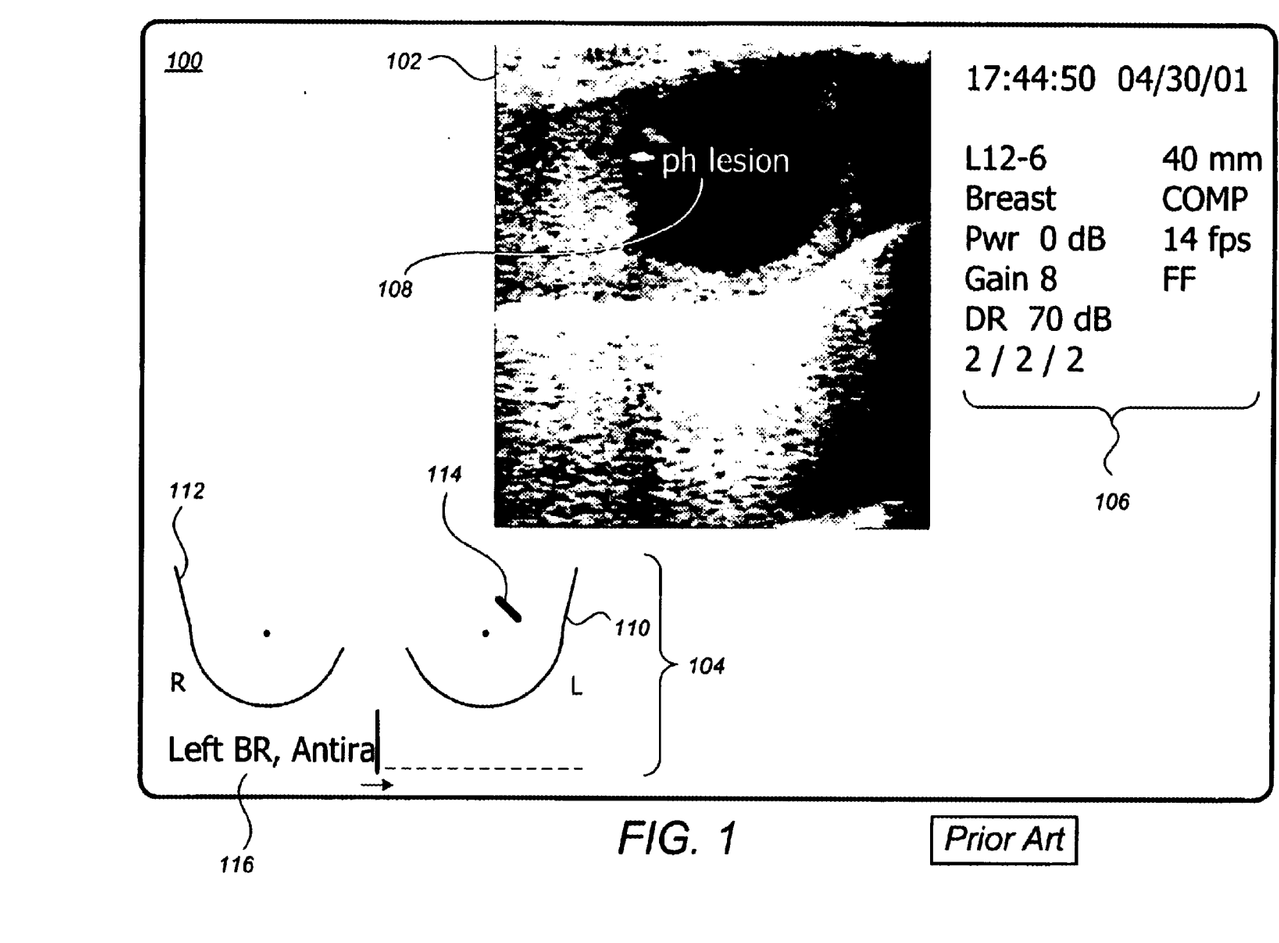
FIG. 1 illustrates a prior art ultrasound display output.

FIG. 1 shows a conventional ultrasound display 100 comprising an ultrasound image 102, a body marker region 104, other ultrasound parameters 106, and a user-typed text string 108. Body marker region 104 has the important purpose of illustrating to a subsequent viewer the position of the ultrasound probe when the ultrasound image 102 was taken. Body marker region 104 comprises left and right breast icons 110 and 112, respectively, against which a movable probe icon 114 is manipulated by the user to reflect the current position of the ultrasound probe. Most commonly, a trackball input is used to manipulate the location of probe icon 114 relative to the breast icons, while a probe orientation knob is rotated to manipulate the orientation of the probe icon 114 relative to the breast icons. Other ultrasound parameters 106 is a text display of relevant parameters such as time, date, probe power, frame rate, etc.

User-typed text string 108, shown in FIG. 1 by the characters "ph lesion" (representing the term "phantom lesion"), is input by the user by positioning a freely movable text cursor, using a trackball, to the relevant location on the ultrasound output 100 and then entering the relevant text portion. This is usually done to point out certain aspects of the ultrasound image 102 that may be interesting to a subsequent viewer but that may, or may not, be immediately apparent to the subsequent viewer.

Finally, ultrasound display 100 comprises a probe position text sequence 116 placed within the body marker region 104. In conventional systems, the probe position text sequence 116 is typed in by the user, using the same or similar text input mode that is used to enter the user-typed text string 108. The probe position text sequence 116 is shown in FIG. 1 as having been only partially input, with a cursor moving to the right as it is typed in by the user. The probe position text sequence 116 is intended to textually communicate the position of the ultrasound probe as graphically expressed by the location and orientation of the probe icon 114. As used herein, the term "location" refers to the x-y placement of the ultrasound probe/probe icon (and also the z coordinate if applicable). The term "orientation" refers to the direction in which probe icon/ultrasound probe transducer array is pointed. The term "position" refers to the collective location and orientation information.

As known in the art, typical examples of probe position text sequence 116 may include: (i) "Left BR, Antiradial, 1:30, 3 cm," meaning that the probe is over the left breast, is at a radius of 3 cm from the left nipple at an angle of 1:30 (i.e., 45 degrees from vertical using clock coordinates), and has an orientation in the antiradial direction (i.e., is tangent to a circle centered on the left nipple at the 1:30 location); (ii) "Left BR, Radial, 6:00, 5 cm," meaning that the probe is located over the left breast 5 cm directly below the left nipple and is oriented in the radial direction, (iii), "Right BR, Trans, 10:00, 4 cm," meaning that the probe is located over the right breast at 4 cm in the 10:00 direction from the right nipple and is oriented in the transverse direction (i.e., parallel to a line between the two breast nipples), (iv) "Right BR, Long, 7:00, 8 cm," meaning that the probe is over the right breast at 8 cm in the 7:00 direction and is oriented in the longitudinal direction (i.e., parallel to the longitudinal or sagittal axis of the body), and (v) "Left BR, Oblique, 8:00, 3 cm" meaning that the probe is over the left breast at 3 cm in the 3:00 direction, and is not oriented along any standard direction. As known in the art, examples (i) and (ii) above express the orientation of the probe with respect to a radial/antiradial coordinate system, while examples (iii) and (iv) express the orientation of the probe with respect to a transverse/longitudinal coordinate system. In general, the "oblique" designation in example (v) may be used with either the radial/antiradial or transverse/longitudinal coordinate system.

One problem that arises with the system of FIG. 1 is that the user is required to alphanumerically key in the probe position text sequence 116 when such text is desired. This process can be cumbersome, can lead to user frustration, and, when many breast ultrasound scans are being recorded, can lead to user fatigue. Sonographers must routinely manipulate the ultrasound probe with one hand and operate the ultrasound system controls and keyboard with the other. The hand that manipulates the probe is often times gloved and/or encumbered by having ultrasound gel on it. With interventional procedures including biopsies and ductography, contamination may occur from blood and/or nipple discharge as well. Conventional annotation mechanics that require any keyboard entries mean that the operator either has to stop, wipe their hands, and then type with both hands, or, use a keyboard designed for two hands with a single hand. Further, unless the operator truly goes to the sink and washes thoroughly and carefully before typing on the keyboard, there is the potential for contamination of the keyboard with pathogens such as fomites. These could be passed on to later patients by the operator. Also, there is the potential for damage of the equipment by moisture from the ultrasound gel deposited on the keyboard and controls.

Moreover, any delays incurred while typing in the probe position text sequence 116 can lead to the possibility that the ultrasound probe may have moved slightly in the meantime. Due to frustration, fatigue, or other factors, the user may return to properly adjust the probe icon 114 and the probe position text sequence 116. This can result in decreased correlation between the ultrasound image and the supporting information the printed or digitally stored copy.

Another disadvantage of the system of FIG. 1 is that different users may incorporate different text schemes for entering the probe position text sequence 116, or the same user may use different text schemes at different times. As a result, different ultrasound output pages from the same laboratory or even the same user may differ in the format of their probe position text sequences. Especially in environments in which such information would be digitally stored, this is disadvantageous because it makes statistics gathering or other off-line automated analysis difficult to achieve across large volumes of ultrasound outputs. Given the potential future usefulness of such information in tracking historical data associated with different patients or populations, it may be important to ensure uniformity in the probe position text sequences of ultrasound output pages.

Finally, another disadvantage of the system of FIG. 1 is that even the purely graphical manipulation of the probe icon 114 may be cumbersome if the user wished the ultrasound probe position to remain in a major direction. For example, if the user is recording two successive ultrasound frames in the antiradial orientation at two different locations, then after the first frame the user must move the trackball until the probe icon is at the second location, and then must carefully re-manipulate the probe orientation knob until the probe icon is oriented in the antiradial direction. This process is unnecessarily cumbersome when it is already known that the probe icon should be in the antiradial direction at the second location.

While a completely automatic position sensing system might represent one option for providing an automatic recording of probe position information, including text-based information, it has been found that position sensing equipment can be cumbersome to use in clinical applications. Moreover, the accuracy of such systems can be reduced because the patient's breast nipples, used as reference points in the probe position display, often move around during the ultrasound procedure. This reduces the usefulness of the position sensor readouts as replacements for the medical professional's own estimation of probe position.

Accordingly, it would be desirable to provide an ultrasound system that is easier to use in terms of the textual recordation of user estimates of ultrasound probe position.

It would be further desirable to provide an ultrasound system that is easier to use in terms of orientating a probe icon along major directions while manipulating the probe icon.

It would be still further desirable to provide an ultrasound system that promotes uniformity in the formatting of probe position text sequence outputs.

It would be even further desirable to provide an ultrasound system for which the user can functionally operate the controls efficiently and ergonomically with one hand.

SUMMARY

In accordance with a preferred embodiment, a method and system for providing ultrasound probe position information corresponding to an ultrasound image of a target are provided, wherein a text sequence corresponding to a user's estimate of the position of an ultrasound probe is automatically generated based on the user's graphical manipulations of a probe icon relative to a breast icon. User inputs are received through a trackball, knob, mouse, or other graphical input device and used to adjust the position of the probe icon relative to the breast icon. The probe position text sequence is automatically generated and continuously updated as the probe icon is manipulated. Because the user is no longer required to manually key in their estimate of the probe position, they may concentrate more easily on accurate placement of the probe icon on the ultrasound display. Moreover, user fatigue associated with repeated keypad entries is avoided. Additionally, probe position text sequences are generated in a common format without unnecessary truncations or misspellings, thereby being more amenable to digital archiving and subsequent computerized access and analysis.

In one preferred embodiment, the user is permitted to select a snapping mode of operation in which the probe icon is snapped to align with a major direction of a preselected coordinate system. In one particular preferred embodiment, this snapping mode is automatically associated with the user's selection of a radial/antiradial coordinate system, for which this snapping mode has been found to be particularly useful and convenient. If the preselected coordinate system is the transverse/longitudinal coordinate system, this snapping mode is not automatically activated, for permitting a large range of oblique orientations to be recorded.

In another preferred embodiment, the user is permitted to select a classification mode of operation in which the location of the probe icon is automatically classified into one of a plurality of standardized zones based on its position with respect to a reference point, such as a nipple of the patient's breast. A text representation of this zone is included in the probe position text sequence. Optionally, the user is permitted to select a manual override mode of operation in which the probe position text sequence may be altered or appended by the user.

DETAILED DESCRIPTION

Figure 2A:
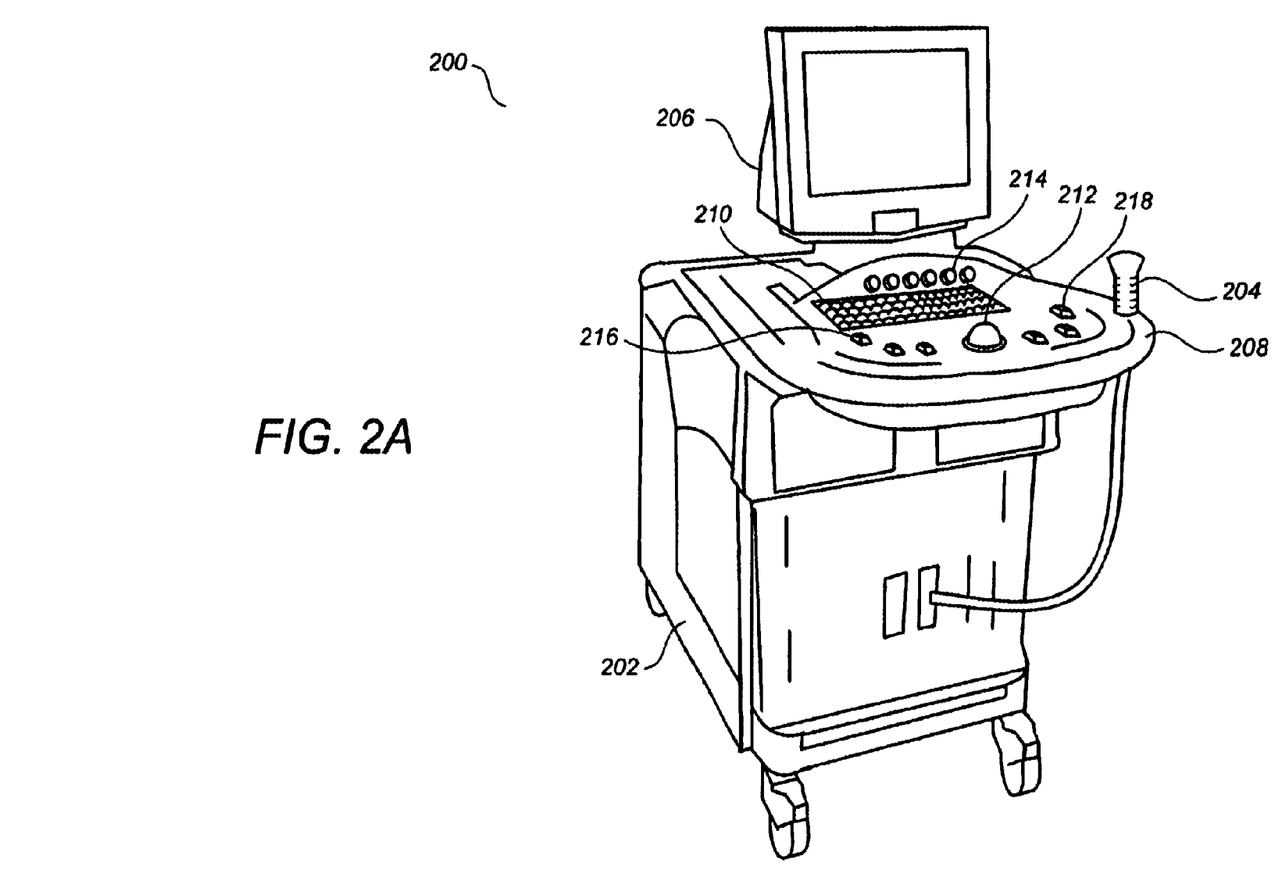
FIG. 2A illustrates an exterior view of an ultrasound system in accordance with a preferred embodiment.

FIG. 2A illustrates an exterior view of an ultrasound system 200 in accordance with a preferred embodiment, the ultrasound system 200 being amenable for recording probe positions during breast ultrasound scans in accordance with a preferred embodiment. In one preferred embodiment, the ultrasound system 200 is similar to an ultrasound system currently named the USI-2000™ available from U-Systems, Inc. of San Jose, Calif. It is to be appreciated, however, that many ultrasound system architectures may be readily adapted for use in accordance with the preferred embodiments.

Ultrasound system 200 comprises a chassis 202 for housing ultrasound processing hardware, an ultrasound probe 204, a monitor 206, and a user interface platform 208. User interface platform 208 comprises a keyboard 210, a trackball 212, a series of rotatable knobs including a probe orientation knob 214, and a plurality of user buttons or keys including a body marker key 216 and a set key 218.

Figure 2B:
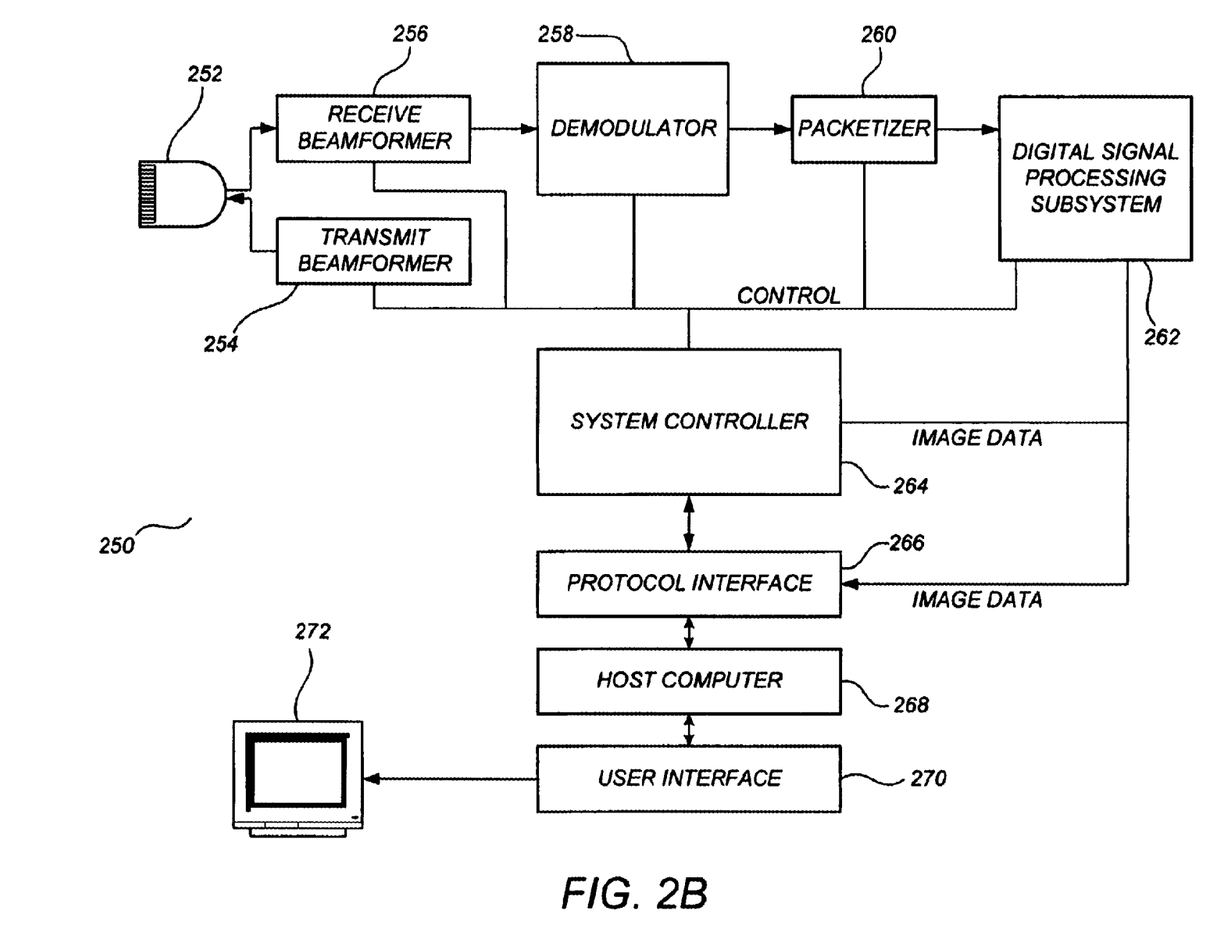
FIG. 2B illustrates a functional block diagram of an ultrasound system in accordance with a preferred embodiment.

FIG. 2B illustrates a functional block diagram of an ultrasound system 250 that generally corresponds to the ultrasound system 200 of FIG. 2A. Ultrasound system 250 comprises a transducer 252, a transmit beamformer 254, a receive beamformer 256, a demodulator 258, a packetizer 260, a digital signal processing (DSP) subsystem 262, a system controller 264, a protocol interface 266, a host computer 268, a user interface 270, and a display 272. Although many ultrasound system architectures may be readily adapted for use in accordance with the preferred embodiments, ultrasound system 250 is preferably similar to the those described in the commonly assigned U.S. Ser. No. 09/224,635, filed Dec. 31, 1998, and U.S. Ser. No. 09/449,095 filed Nov. 24, 1999, which are incorporated herein by reference, or to the USI-2000™ system, supra.

Transducer 252 comprises an array of transducer elements that transmits focused acoustic signals into a target responsive to signals generated by the transmit beamformer 254. Responsive to control signals and parameters received from system controller 264, transmit beamformer 254 generates signals that are converted into acoustic interrogation signals by transducer 252 and introduced into the target. Transducer 252 also receives acoustic echoes from the target and converts them into signals for forwarding to receive beamformer 256. Receive beamformer 256 receives the signals and converts them into a single-channel RF signal. Demodulator 258 receives the single-channel RF signal and generates component frames therefrom, which are then packetized by packetizer 260 and fed to DSP subsystem 262. DSP subsystem 262 performs any of a variety of image processing algorithms on the packetized component frames (e.g., filtering, image compounding, segmentation, etc.) in accordance with the flexible, programmable architecture of the ultrasound system 250. The output image data is transferred to protocol interface 266, but may optionally be further processed by system controller 264. The compound output image frames are then transferred to host computer 268 which performs scan conversion on the signals for transmission to user interface 270 and ultimate display by display 272.

In one preferred embodiment, the host processor 268 and user interface 270 comprise off-the-shelf Intel-based hardware running a Windows NT operating system, and execute instructions compiled from one or more programs written in the C++ programming language to achieve the functions described herein. However, it is to be appreciated that probe position detection and recording in accordance with the preferred embodiments may be implemented on any of a variety of computing platforms. Indeed, in one preferred embodiment, probe position detection and recording may even be implemented on a computer system separate from the ultrasound system 250, provided that the user may simultaneously view their respective outputs, and provided that hardcopy or digital storage outputs of the separate systems may be properly associated with each other. Given the present disclosure, a person skilled in the art will be readily able to implement a computer program or group of programs for achieving the functionalities described herein.

FIGS. 3A–3D show a body marker region 300 of an ultrasound display in accordance with a preferred embodiment. Body marker region 300 comprises a right breast icon 302, a left breast icon 304, a probe icon 306, and a probe position text sequence 308. In accordance with a preferred embodiment, probe position text sequence 308 is automatically and continuously generated and displayed based on the position of the probe icon 306. Probe icon 306, in turn, is manipulated by the user through trackball 212 and probe orientation knob 214 according to the user's estimate of the position of the actual ultrasound probe, which the user is usually holding in their other hand. Probe position text sequence 308 is generated using conventional geometrical principles together with a scaling factor that scales distances on the body marker region 300 to actual physical distances on the patient's body. Usually, a fixed approximation that the breast nipples are separated by about 30 cm will suffice for computing the scaling factor, although this distance may be user-settable.

Figure 3A:
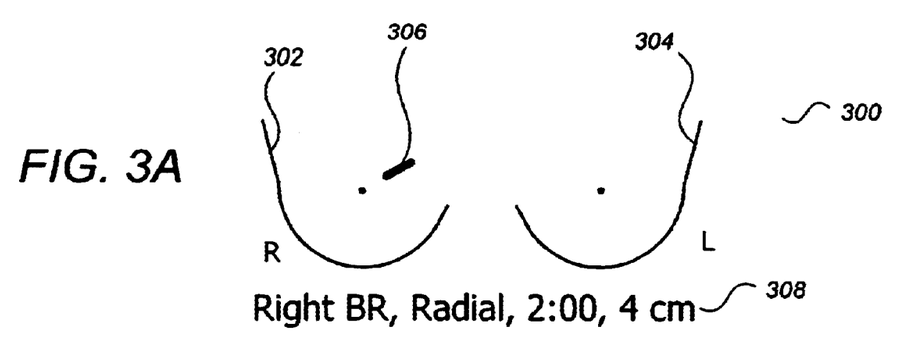
FIGS. 3A–3D illustrate a body marker portion of an ultrasound display output in accordance with a preferred embodiment.
Figure 3B:
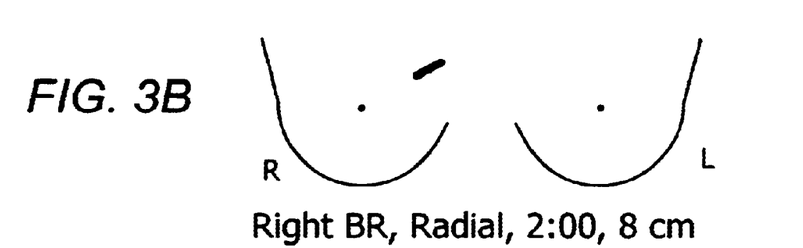
Figure 3C:
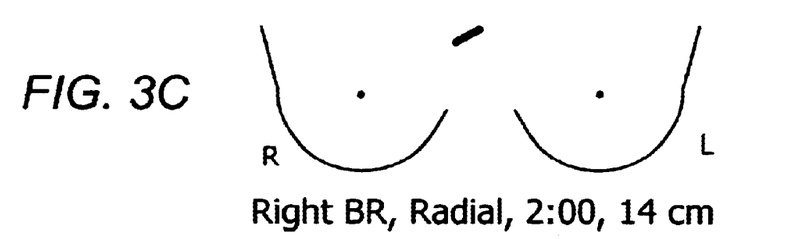
Figure 3D:
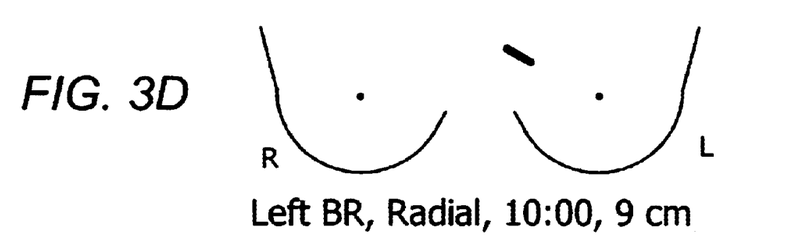

FIGS. 3A–3D represent a sequence of configurations of the body marker region 300 as the user changes the location of the probe icon 306 from its location in FIG. 3A to its location in FIG. 3D, with the user having chosen a radial/antiradial mode of operation. In this mode of operation, the probe icon 306 is automatically snapped to the closer of the radial or antiradial direction prior to display and prior to computation of the probe position text sequence 308. If the location remains fixed while the user turns the probe orientation knob 214 continuously, the probe icon 306 will remain fixed in its orientation (radial or antiradial) as the probe orientation knob 214 subtends a small arc around its current position. However, when a threshold arc is reached, the probe icon 306 will snap ninety degrees to align with the next major direction (antiradial or radial, respectively).

In the example of FIGS. 3A–3D, the probe icon 306 begins in a radial orientation at 2:00 in FIG. 3A, and the user moves the trackball to the right and slightly up such that the probe icon remains generally along the 2:00 direction with respect to the nipple of the right breast icon 302. As the probe icon 306 moves, the probe position text sequence 308 continuously changes (see FIGS. 3B and 3C) to reflect its current position. In accordance with a preferred embodiment, the text sequence portion corresponding to the angular location only changes by preselected increments, e.g. in ½ hour or 1 hour increments. This is in recognition that the precision of the user's estimation of the angular location of the ultrasound probe will usually not be finer than these amounts. Thus, while the angular location of the probe icon 306 with respect to the nipple of the right breast icon 302 may wander somewhat from the precise 2:00 direction, the text will still read 2:00.

In the example of FIGS. 3A–3D, the orientation of the probe icon 306 remains snapped to the radial direction. If the initial orientation of the probe icon 306 were in the antiradial direction, the antiradial orientation would remain regardless of probe icon location, the probe icon 306 rotating on its own so that it faces the nipple of the right breast icon. The probe icon 306 will continue to do so until the user turns the probe orientation knob 214 by an amount sufficient to snap the probe icon 306 to the radial direction. This feature has been found to particularly enhance ease-of-use of the system by reducing the required manipulation of the probe orientation knob when the user wishes the ultrasound probe to remain aligned with a major (radial/antiradial) direction.

In contrast, where the transverse/longitudinal mode is selected, the probe orientation will remain fixed with respect to the output display screen unless probe orientation knob 214 is turned. Different amounts, increments, and directions of snapping may of course be implemented without departing from the scope of the preferred embodiments.

FIGS. 3C–3D show the crossover of the probe icon 306 from the right breast to the left breast. In accordance with a preferred embodiment, ultrasound system 200 automatically detects which breast icon nipple is nearer to the probe icon 306, and uses that nipple as the reference point for generating the probe position text sequence 308. As the probe icon 306 changes over to the left breast coordinate system, it is automatically rotated and snapped to its new radial orientation (from 2:00 to 10:00).

Figure 4:
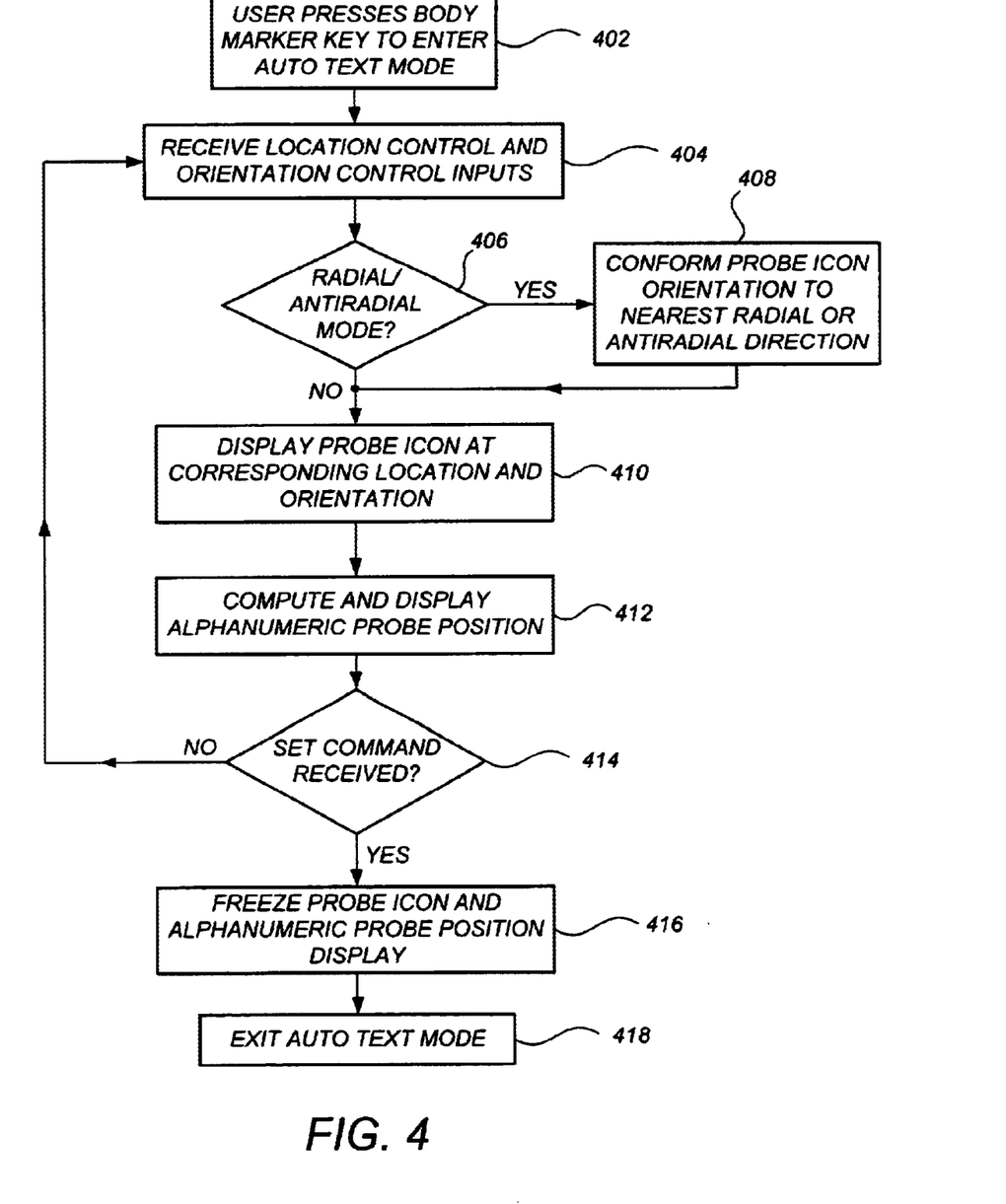
FIG. 4 illustrates steps for recording probe position during a breast ultrasound scan in accordance with a preferred embodiment.

FIG. 4 illustrates steps taken in a method for recording probe position during breast ultrasound scans in accordance with a preferred embodiment. At step 402, the user presses the body marker key 216 to enter into the auto text mode. At this point, the probe position text sequence will begin to continuously appear in an updated fashion in the body marker region. At step 404, ultrasound system 200 receives location control and orientation control inputs using the graphical inputs described supra. If the user has selected the radial/antiradial mode in a setup screen described infra, the probe icon will be snapped to the nearest radial or antiradial orientation (steps 406 and 408). At steps 410 and 412, the probe icon is displayed along with the automatically-computed probe position text sequence. At step 414, if a set command is not received, further graphical user inputs are received at step 404. If a set command is received at step 414, step 416 is executed in which the probe icon and probe position text sequence are frozen, and the auto text mode is exited at step 418. At this point, the user may invoke a print command or other output command to cause the screen ensemble to be printed on a printer or digitally stored. In one preferred embodiment, the user may be given the option, before or after exiting the auto text mode, of altering or appending the probe position text sequence.

Figure 5:
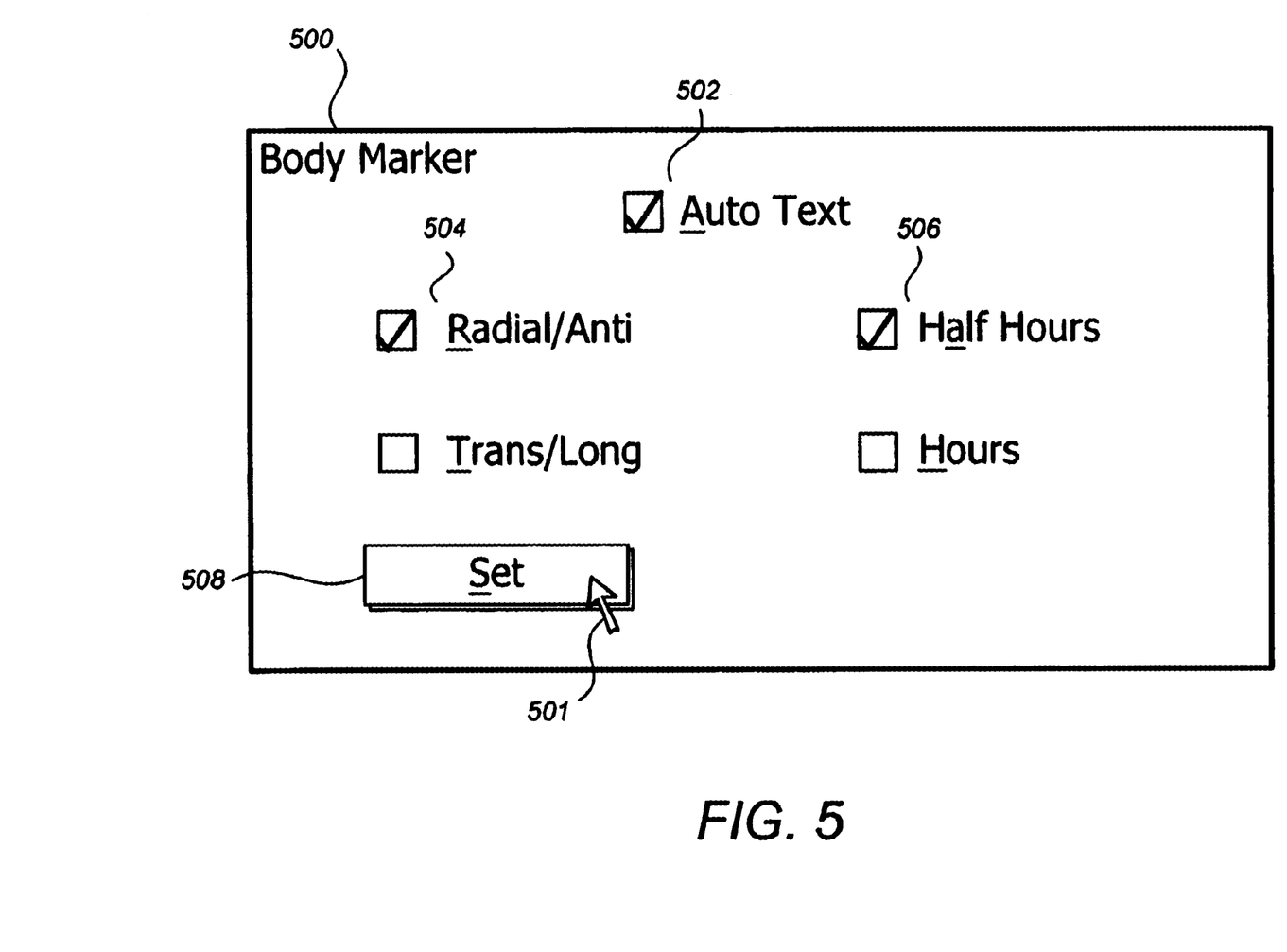
FIG. 5 illustrates an input screen for setting alphanumeric probe position display parameters in accordance with a preferred embodiment.

FIG. 5 shows an auto text setup screen 500 in accordance with a preferred embodiment, comprising an activation toggle 502, a coordinate system selection column 504, an angular location precision selection column 506, and a set button 508. Auto text setup screen 500 conveniently allows the user, using a conventional personal-computer-like display with a mouse icon 501, to enable/disable the auto text feature, and to pre-select the desired settings among coordinate system options and angular location precision options described supra.

In an optional preferred embodiment, the user is permitted to select a classification mode of operation in which the location of the probe icon is automatically classified into one of a plurality of standardized zones based on its position with respect to the reference point, such as a nipple of the patient's breast. A text representation of the zone is then included in the probe position text sequence. By way of example and not by way of limitation, some users prefer the annotation of Zone 1, 2, and 3 to represent successive concentric rings having widths of one-third of the radius of the breast, with Zone 1 being nearest the nipple and zone three being farthest from the nipple. A typical probe position text might read "Left BR, Antiradial, 8:00, 6 cm, Zone 2" or simply "Left BR, Antiradial, 8:00, Zone 2."

In another optional preferred embodiment, the zone classification may also include depth information. Most commonly, this depth information would apply to a particular lesion or other important feature appearing in the ultrasound image. For example, a depth classification A, B, or C may be added to represent the anterior third, middle third, or posterior third of the region between the skin surface of the patient's breast and the pectoral muscle underneath the patient's breast. Several different methods may be used to generate this data point. In a first example, ultrasound system settings corresponding to a focus depth may be imported to compute the depth classification, it being assumed that the user will cause the lesion to be placed at the focus depth. In a second example, the user would manipulate two cursor marks superimposed on the ultrasound image itself, one at the center of the lesion and the other at the surface of the pectoral muscle. The ultrasound system would then automatically compute the proper depth classification. In a third example, a vertical profile icon having a top marker representing the skin surface and a bottom marker representing the pectoral muscle may be displayed adjacent to the breast body marker supra. The user may then place a cursor at the appropriate place between the top and bottom markers of the vertical profile icon, whereby the ultrasound system may then automatically compute a depth classification A, B, or C. The second and third examples recognize the fact that the depth of the pectoral muscle differs from patient to patient depending on their breasts size and other factors. By way of example, in this embodiment, a typical probe position text sequence might read "Left BR, Antiradial, 8:00, 6 cm, Zone 2B" or simply "Left BR, Antiradial, 8:00, Zone 2B".

Advantageously, a system according to the preferred embodiments makes accurate and fast annotation possible with one hand. Among other benefits, this allows the operator to keep their gloved, scanning hand away from the ultrasound machine once the patient demographics have been entered and the examination has begun. This minimizes the potential for contamination of the ultrasound unit and the spread of pathogens from patient to patient. In additional to cleanliness benefits, both ergonomics and biomechanical efficiency are improved. Because there is less typing involved overall, the likelihood of biomechanical injury that can result from repetitive keyboard entry (e.g., carpal tunnel syndrome) is reduced.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, while presented supra in the context of breast ultrasound scans, the preferred methods for recording ultrasound probe position are readily adaptable to other ultrasound applications, including pre-natal ultrasound applications, other medical ultrasound applications, non-medical ultrasound applications (e.g., for manufacturing quality control, etc.), and other medical imaging applications. Additionally, the features and advantages of the preferred embodiments are readily adaptable for wider use with PACS and teleradiology systems, supra, where images acquired elsewhere are to be further annotated on a remote workstation using a keyboard, perhaps at the time of interpretation. Therefore, reference to the details of the preferred embodiments are not intended to limit their scope, which is limited only by the scope of the claims set forth below.

What is claimed is:

1. A method for providing ultrasound probe position information relating to an ultrasound image of a target, comprising the steps of:
displaying a target icon to a user;
displaying a probe icon to the user;
receiving input signals from the user that manipulate a position of said probe icon relative to said target icon, said probe icon position corresponding to a user estimate of an actual ultrasound probe position relative to the target;
using said ultrasound probe icon position to compute an alphanumeric sequence describing said user estimate of the actual ultrasound probe position; and
displaying said alphanumeric sequence to the user for real-time viewing in conjunction with the ultrasound image;
whereby said alphanumeric sequence describing said user estimate of the actual ultrasound probe position is generated without requiring manual alphanumeric entry thereof by the user.

2. The method of claim 1, said probe icon position being characterized by (i) location coordinates relative to a target icon reference point indicative of a reference point on the target, and (ii) orientation information relative to a preselected coordinate system.

3. The method of claim 2, said target comprising a breast area of a patient's body including left and right nipples thereof, said target icon comprising left and right nipple icons corresponding to said left and right nipples, respectively, further comprising the steps of:
determining which of said left or right nipple icons is nearer to said probe icon; and
using the nearer nipple icon as the target icon reference point.

4. The method of claim 3, wherein said preselected coordinate system is selected by the user from choices comprising a transverse/longitudinal system and a radial/antiradial system.

5. The method of claim 4, further comprising the step of snapping the orientation of said probe icon to align with a major direction of the preselected coordinate system.

6. The method of claim 4, further comprising the steps of:
if the preselected coordinate system is the radial/antiradial system:
snapping the orientation of said probe icon to align with one of the radial direction or the antiradial direction; and
expressing the orientation of said probe icon in said alphanumeric sequence in terms of said snapped orientation; and
if the preselected coordinate system is the transverse/longitudinal system:
snapping the orientation of said probe icon to align with one of the transverse direction or longitudinal direction only if the probe orientation is close to these orientations; and
expressing the orientation of said probe icon in said alphanumeric sequence in terms of said snapped orientation if said probe icon has been snapped, or as an oblique direction if said probe icon has not been snapped.

7. The method of claim 3, further comprising the step of:
classifying the location of the probe icon into one of a plurality of standardized zones around the nearer nipple icon; and
including the standardized zone into which the probe icon location has been classified into said alphanumeric sequence.

8. The method of claim 2, further comprising the steps of:
freezing the position of the probe icon responsive to a set command received from the user; and
outputting the ultrasound image and the alphanumeric sequence to an output device responsive to an output command received from the user.

9. The method of claim 8, wherein said output device is selected from the group consisting of hardcopy output devices and digital information storage devices.

10. The method of claim 1, wherein said input signals are received from the user through one or more graphical input devices selected from the group consisting of: track ball devices, mouse devices, circular knobs, linear knobs, position buttons, and toggle buttons.

11. An apparatus for use with a breast ultrasound imaging system, said breast ultrasound imaging system generating ultrasound images responsive to scans taken by an ultrasound probe under the control of a user, comprising:
a first display area for displaying a breast body marker and a probe icon to the user;
a graphical input device for receiving graphical input commands from the user that manipulate the location and orientation of the probe icon relative to the breast body marker in a way that reflects the user's estimation of a current location and orientation of the ultrasound probe relative to a patient; and
a processor programmed to compute, using the current location and orientation of the probe icon relative to the breast body marker, a text sequence that describes the user's estimation of the current location and orientation of the ultrasound probe relative to the patient; and
a second display area for displaying said text sequence to the user.

12. The apparatus of claim 11, said breast body marker comprising left and right nipple icons representative of the left and right nipples of the patient, respectively, said text sequence comprising distance information computed by (i) determining a spacing between the probe icon and that left or right nipple icon that is nearer to the probe icon, and (ii) multiplying that spacing by a scaling factor.

13. The apparatus of claim 12, said text sequence further comprising angle information that, together with said spacing, describes the position of said probe icon relative to said nearest nipple icon.

14. The apparatus of claim 13, said text sequence further comprising orientation information that describes the orientation of the probe icon relative to a preselected coordinate system, said preselected coordinate system being selected from the group consisting of a radial/antiradial system and a transverse/longitudinal system.

15. The apparatus of claim 14, wherein said probe icon is snapped to a major direction of said preselected coordinate system prior to generation of said text sequence.

16. The apparatus of claim 15, said processor being further programmed to classify the location of the probe icon into one of a plurality of predetermined zones around said nearer nipple icon, and to include the resulting classification in said text sequence.

17. A computer program product on a recordable medium for use in an ultrasound imaging system, comprising:
computer code for displaying a target icon to a user;
computer code for displaying a probe icon to the user;
computer code for receiving input signals from the user that manipulate a position of the probe icon relative to the target icon, the probe icon position corresponding to a user estimate of the position of an actual ultrasound probe being manipulated by the user relative to an actual target;

computer code for using said ultrasound probe icon position to compute an alphanumeric sequence describing said user estimate of the actual ultrasound probe position; and computer code for displaying said alphanumeric sequence to the user for viewing in conjunction with an ultrasound image corresponding to the actual ultrasound probe position;

whereby said alphanumeric sequence describing said user estimate of the actual ultrasound probe position is generated without requiring manual alphanumeric entry thereof by the user.

18. The computer program product of claim 17, said probe icon position being characterized by (i) location coordinates relative to a target icon reference point indicative of a corresponding reference point on the actual target, and (ii) orientation information relative to a preselected coordinate system.

19. The computer program product of claim 18, said actual target comprising a breast area of a patient's body including left and right nipples thereof, said target icon comprising left and right nipple icons corresponding to said left and right nipples, respectively, further comprising:

computer code for determining which of said left or right nipple icons is nearer to said probe icon; and computer code for using the nearer nipple icon as the target icon reference point.

20. The computer program product of claim 19, wherein said preselected coordinate system is selected by the user from choices comprising a transverse/longitudinal system and a radial/antiradial system.

21. The computer program product of claim 20, further comprising computer code for snapping the orientation of said probe icon to align with a major direction of the preselected coordinate system.

22. The computer program product of claim 20, further comprising:

computer code for performing the following steps if the preselected coordinate system is the radial/antiradial system:

snapping the orientation of said probe icon to align with one of the radial direction or the antiradial direction; and expressing the orientation of said probe icon in said alphanumeric sequence in terms of said snapped orientation; and computer code for performing the following steps if the preselected coordinate system is the transverse/longitudinal system:

snapping the orientation of said probe icon to align with one of the transverse direction or longitudinal direction only if the probe orientation is close to these orientations; and expressing the orientation of said probe icon in said alphanumeric sequence in terms of said snapped orientation if said probe icon has been snapped, or as an oblique direction if said probe icon has not been snapped.

23. The computer program product of claim 19, further comprising:

computer code for classifying the location of the probe icon into one of a plurality of standardized zones around the nearer nipple icon; and computer code for including the standardized zone into which the probe icon location has been classified into said alphanumeric sequence.

24. The computer program product of claim 18, further comprising:

computer code for freezing the position of the probe icon responsive to a set command received from the user; and computer code for outputting the ultrasound image and the alphanumeric sequence to an output device responsive to an output command received from the user.

25. The computer program product of claim 24, wherein said output device is selected from the group consisting of hardcopy output devices and digital information storage devices.

26. The computer program product of claim 17, said computer program product being adapted to receive said input signals from the user through one or more graphical input devices selected from the group consisting of: track ball devices, mouse devices, circular knobs, linear knobs, position buttons, and toggle buttons.

27. A method for automatically creating and displaying alphanumeric information indicative of relative positions of an imaging probe and a body being imaged with the probe, comprising:

displaying to a user at a first display area (a) a body icon representing the body being imaged, and (b) a probe icon representing the probe;

computer-processing information from the user manipulating a graphical computer input device to both (a) show relative movement of said probe icon and body icon at said first display, and (b) generate alphanumerical information indicative of relative positions of said probe and body; and displaying said alphanumerical information to the user at a second display area.

28. A method as in claim 27 in which said computer-processing comprises generating said alphanumerical information in a preset format.

29. A method as in claim 28 in which said computer-processing comprises selecting said preset format from a selection of different preset formats that use different units indicative of distance or location.

30. A method as in claim 27 in which said computer-processing comprises generating alphanumeric information indicative of both location and orientation of the probe relative to a selected point in the body.

* * * * *